United States Patent [19]

Saville

[11] Patent Number: Plant 6,053

[45] Date of Patent: Dec. 8, 1987

[54] ROSE PLANT NAMED SAVAMAE

[75] Inventor: F. Harmon Saville, Rowley, Mass.

[73] Assignee: Nor'East Miniature Roses, Inc., Rowley, Mass.

[21] Appl. No.: 801,699

[22] Filed: Nov. 25, 1985

[51] Int. Cl.[4] ..... A01H 5/00

[52] U.S. Cl. ..... Plt./7

[58] Field of Search ..... Plt. 7

*Primary Examiner*—Robert E. Bagwill

*Attorney, Agent, or Firm*—Vincent G. Gioia

[57] ABSTRACT

A new miniature rose variety of unusual carrot red coloring having good exhibition form.

1 Drawing Figure

The present invention relates to a new and distinct variety of rose plant of the miniature rose class, which was originated by my crossing as seed parent the rose known as "Zorina" (U.S. Plant Pat. No. 2,321) and as pollen parent an unpatented, unnamed seedling of my creation. The varietal denomination of this new variety is "Savamae".

Among the novel characteristics possessed by this new variety which distinguish it from its parents and all other varieties of which I am aware are its attractive and unusual carrot red colored flowers of good exhibition form that maintain their color and form through development and aging. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "29A" is plate 29A of The Royal Horticultural Society Colour Chart.

Parentage: Seedling.

*Seed parent.*—"Zorina".

*Pollen parent.*—Unnamed, unpatented seedling.

Class: Miniature.

The following observations are made of specimens grown outdoors in Essex County, Mass., during the month of August.

FLOWER

Blooming habit: Near continuous.

A. Bud:

(1) *Size.*—Medium.

(2) *Form.*—Long, pointed, high centered.

(3) *Color.*—Before sepals divide first indication of color is near 29A (carrot red); after sepals fall, petal undersurface of lighter tonality, near 29B to 29C is evident. However, lower petal segments near point of petal attachment appear to have some yellowish cast.

(4) *Sepals.*—Slightly longer than bud, lightly foliated, lightly glandular.

(5) *Peduncle.*—Length — about $\frac{5}{8}$ to $\frac{3}{4}$ inch. Aspect — straight. Strength — erect. Color — near 143C.

B. Bloom:

(1) *Size.*—Average size when fully expanded — about $1\frac{1}{4}$ to $1\frac{3}{4}$ inches.

(2) *Borne.*—Singly and several together in sprays of three to five flowers.

(3) *Form.*—High centered at first, becoming flat, outer petals reflex to point and inner petals roll under upon opening but with pointed apices.

(4) *Petalage.*—Number of petals under normal conditions — about 35.

(5) *Color.*—After sepals fall and as flower opens, outer petals quill to points and some inner petals roll under. Flower coloring at one-half open stage is a blend of 29A, 29B and 29C, approaching 31C and 31D. Color of outer petals tends to lighten along petal edge and at apices.

C. Petals (1) *Texture.*—Average.

(2) *Appearance.*—Inside — satiny, outside — satiny.

(3) *Form.*—Broad, fan shaped with pronounced apex on many petals.

(4) *Arrangement.*—Regularly arranged, imbricated.

(5) *Petaloids in center.*—Few.

(6) *Persistence.*—Drop off cleanly.

(7) *Fragrance.*—Slight.

(8) *Lasting quality.*—Very long on plant and as cut flower.

REPRODUCTIVE ORGANS

A. Stamens, filaments and anthers:

(1) *Arrangement.*—Regularly arranged around styles.

(2) *Color.*—Near 17A.

B. Pollen:

*Color.*—Near 17A.

C. Styles: Even length.

D. Stigmas:

*Color.*—Near 154D.

E. Hips: None observed.

PLANT

A. Form: Compact, symmetrical.

B. Growth: Vigorous.

*Height attained.*—About 14 to 18 inches.

C. Foliage: Compound 5 to 7 leaflets.

(1) *Size.*—Medium.

(2) *Quantity.*—Abundant.

(3) *Color.*—New foliage: Upper side — near to 137A. Under side — near to 144A. Old foliage: Upper side — near 139A. Under side — near 139B.

(4) *Shape.*—Oval, pointed.

(5) *Texture.*—Upper side is glossy and under side is matte.

(6) *Edge.*—Serrated.

(7) *Serration.*—Serrate.

(8) *Leaf stem.*—Color — near 183A. Under side — near 146B.

(9) *Stipules.*—Medium, smooth.

(10) *Resistance to disease.*—Blackspot — good. Mildew — good. Rust — good.

D. Wood:

(1) *New wood.*—Color — near 138A. Bark — smooth.

(2) *Old wood.*—Color — near 137A. Bark — smooth.

E. Thorns:

(1) *Thorns.*—Quantity (main stalk) — ordinary. On laterals from stalk — average. Form — long, thin, straight, pointed. Length — medium. Color — near 182A. Position — irregular.

(2) *Prickles.*—None.

F. Winter hardiness: Requires ordinary protection in extreme climates.

I claim:

1. A new and distinct variety of rose plant of the miniature rose class, substantially as shown and described, characterized particularly by unusually attractive carrot red colored flowers of good exhibition form that hold color well through development and aging.

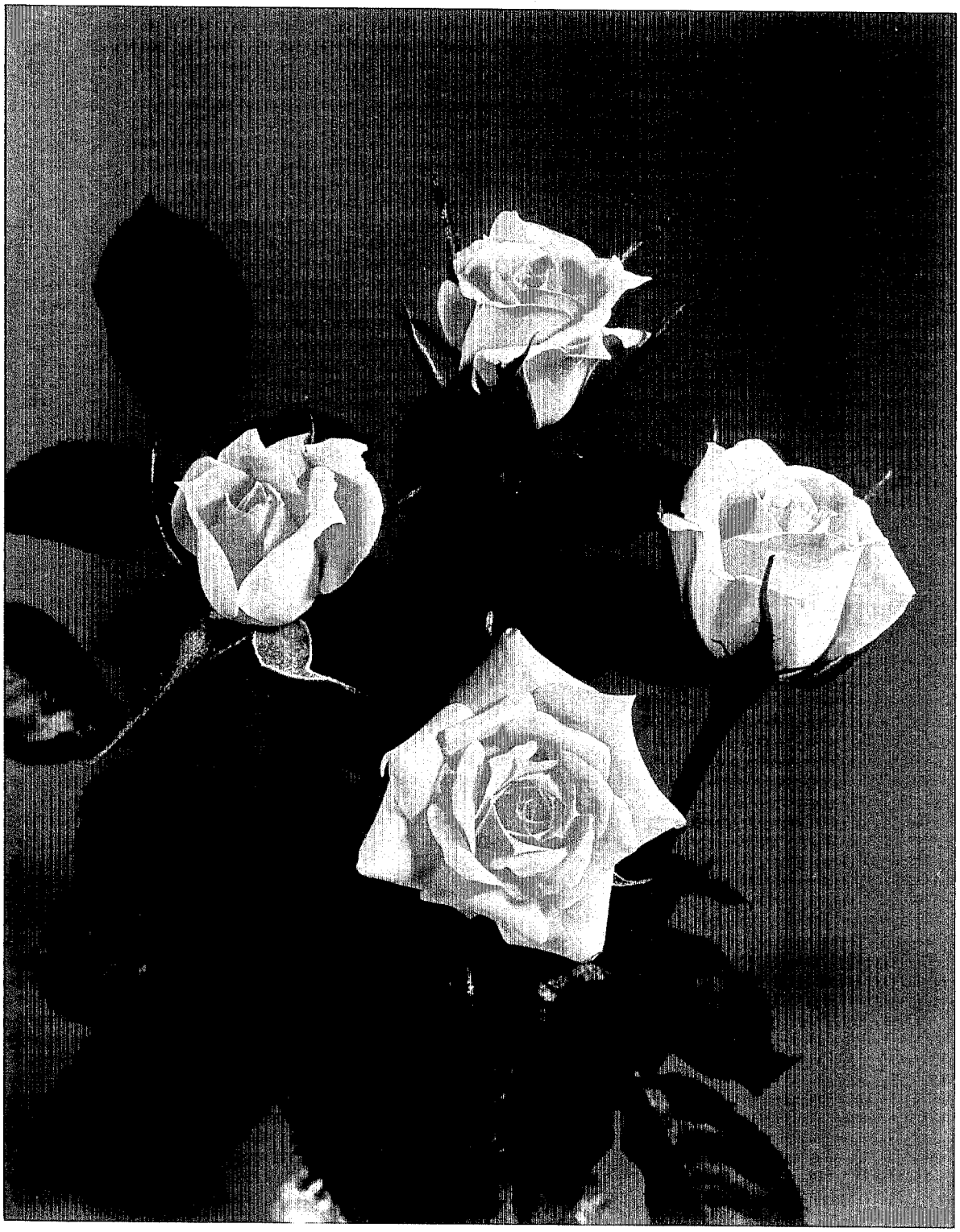

* * * * *